US007883500B2

(12) United States Patent
Levin et al.

(10) Patent No.: US 7,883,500 B2
(45) Date of Patent: Feb. 8, 2011

(54) METHOD AND SYSTEM TO TREAT AND PREVENT MYOCARDIAL INFARCT EXPANSION

(75) Inventors: Howard R. Levin, Teaneck, NJ (US); Mark Gelfand, New York, NY (US)

(73) Assignee: G&L Consulting, LLC, New York, NY (US)

( * ) Notice: Subject to any disclaimer, the term of this patent is extended or adjusted under 35 U.S.C. 154(b) by 1055 days.

(21) Appl. No.: 10/808,397

(22) Filed: Mar. 25, 2004

(65) Prior Publication Data

US 2004/0193138 A1  Sep. 30, 2004

Related U.S. Application Data

(60) Provisional application No. 60/457,246, filed on Mar. 26, 2003.

(51) Int. Cl.
*A61M 31/00* (2006.01)
(52) U.S. Cl. .......................... 604/500; 604/508
(58) Field of Classification Search .............. 604/93.01, 604/96.01, 118, 500, 264, 507–510, 43, 523, 604/915, 920, 131; 128/898, 899; 623/1–3; 600/16–18, 37
See application file for complete search history.

(56) References Cited

U.S. PATENT DOCUMENTS

| | | | |
|---|---|---|---|
| 4,229,299 A | 10/1980 | Savitz et al. | |
| 4,806,355 A | 2/1989 | Goosen et al. | |
| 4,991,578 A * | 2/1991 | Cohen | 607/2 |
| 5,410,016 A | 4/1995 | Hubbell et al. | |
| 5,667,778 A | 9/1997 | Atala | |
| 5,702,343 A | 12/1997 | Alferness | |
| 5,728,134 A | 3/1998 | Barak | |
| 5,900,433 A * | 5/1999 | Igo et al. | 514/530 |
| 5,931,810 A | 8/1999 | Grabek | |
| 5,972,013 A | 10/1999 | Schmidt | |
| 6,077,218 A | 6/2000 | Alferness | |
| 6,085,754 A | 7/2000 | Alferness et al. | |
| 6,095,968 A * | 8/2000 | Snyders | 600/16 |
| 6,123,662 A | 9/2000 | Alferness et al. | |
| 6,126,590 A | 10/2000 | Alferness | |
| 6,155,972 A | 12/2000 | Nauertz et al. | |
| 6,162,195 A | 12/2000 | Igo et al. | |
| 6,165,121 A | 12/2000 | Alferness | |
| 6,165,122 A | 12/2000 | Alferness | |
| 6,174,279 B1 | 1/2001 | Girard | |
| 6,193,648 B1 | 2/2001 | Krueger | |
| 6,206,004 B1 * | 3/2001 | Schmidt et al. | 128/898 |

(Continued)

OTHER PUBLICATIONS

CORCAP Brochure, 2 pages (2004).

(Continued)

*Primary Examiner*—Matthew F DeSanto
(74) *Attorney, Agent, or Firm*—Nixon & Vanderhye P.C.

(57) ABSTRACT

A method and apparatus for prevention and reduction of myocardial infarct expansion and heart remodeling by infusion of fluid into the pericardial space of the heart to created a hydraulic heart constraint. As a result of the constraint ventricular stress and dilation is reduced. Pressure in the pericardial sac is maintained at a safe level for the duration of treatment. Apparatus consists of a catheter and a fluid infusion system.

42 Claims, 6 Drawing Sheets

U.S. PATENT DOCUMENTS

| | | | |
|---|---|---|---|
| 6,217,894 B1 | 4/2001 | Sawhney et al. |
| 6,231,518 B1 | 5/2001 | Grabek |
| 6,241,654 B1 | 6/2001 | Alferness |
| 6,272,930 B1 | 8/2001 | Crozafon et al. |
| 6,293,906 B1 | 9/2001 | Vanden Hoek et al. |
| 6,312,725 B1 | 11/2001 | Wallace et al. |
| 6,332,863 B1 | 12/2001 | Schweich, Jr. et al. |
| 6,332,864 B1 | 12/2001 | Schweich, Jr. et al. |
| 6,352,710 B2 | 3/2002 | Sawhney et al. |
| 6,368,285 B1 | 4/2002 | Osadchy et al. |
| 6,375,608 B1 | 4/2002 | Alferness |
| 6,385,476 B1 | 5/2002 | Osadchy et al. |
| 6,402,679 B1 | 6/2002 | Mortier et al. |
| 6,402,680 B2 | 6/2002 | Mortier et al. |
| 6,416,459 B1 | 7/2002 | Haindl |
| 6,423,051 B1 | 7/2002 | Kaplan et al. |
| 6,425,856 B1 | 7/2002 | Shapland et al. |
| 6,432,119 B1 | 8/2002 | Saadat |
| 6,463,332 B1 | 10/2002 | Aldrich |
| 6,482,146 B1 | 11/2002 | Alferness et al. |
| 6,494,825 B1 | 12/2002 | Talpade |
| 6,500,145 B1 | 12/2002 | Bicakci et al. |
| 6,514,228 B1 | 2/2003 | Hamilton et al. |
| 6,585,635 B1 * | 7/2003 | Aldrich ................ 600/16 |
| 6,592,552 B1 | 7/2003 | Schmidt |
| 6,666,844 B1 | 12/2003 | Igo et al. |
| 6,692,458 B2 * | 2/2004 | Forman et al. ........... 604/93.01 |
| 6,759,431 B2 | 7/2004 | Hunter et al. |
| 6,818,018 B1 | 11/2004 | Sawhney |
| 6,833,408 B2 | 12/2004 | Sehl et al. |
| 7,226,440 B2 | 7/2005 | Gelfand et al |
| 2002/0114775 A1 | 8/2002 | Pathak |
| 2003/0104032 A1 | 6/2003 | Sawhney et al. |
| 2003/0153949 A1 | 8/2003 | Lau et al. |
| 2003/0162841 A1 | 8/2003 | Pathak et al. |
| 2004/0002456 A1 | 1/2004 | Pathak |
| 2004/0009205 A1 | 1/2004 | Sawhney |
| 2004/0143154 A1 | 7/2004 | Lau et al. |
| 2004/0143155 A1 | 7/2004 | Lau et al. |
| 2004/0167558 A1 | 8/2004 | Igo et al. |
| 2004/0219214 A1 | 11/2004 | Gravett et al. |
| 2004/0225077 A1 | 11/2004 | Gravett et al. |
| 2004/0247867 A1 | 12/2004 | Chaouk et al. |
| 2005/0154370 A1 | 7/2005 | Sigg et al. |
| 2005/0165466 A1 | 7/2005 | Morris et al. |
| 2005/0169958 A1 | 8/2005 | Hunter et al. |
| 2005/0169959 A1 | 8/2005 | Hunter et al. |
| 2007/0073218 A1 | 3/2007 | Lau et al. |

OTHER PUBLICATIONS

CORCAP Power Point Presentation, 8 pages (No Date).
Scott T. Kelley, MD et al, "Restraining Infarct Expansion Preserves Left Ventricular Geometry and Function After Acute Anteroapical Infarction", pp. 135-142.
James J. Pilla, PhD, et al., "Ventricular Constraint Using the Acorn Cardiac Support Device Reduces Myocardial Akinetic Area In An Ovine Model of Acute Infarction", pp. I-207-I-211.
Watkins et al, "Physiologic Role of the Normal Pericardium" 44:171-800, Annu. Rev. Med. 1993.
Dictionary Definitions of "Cardiac Tamponade".
Office Action mailed Apr. 13, 2010 from U.S. Appl. No. 11/279,026.
Office Action mailed Apr. 1, 2010 from U.S. Appl. No. 11/282,694.

* cited by examiner

METHOD AND SYSTEM TO TREAT AND PREVENT MYOCARDIAL INFARCT EXPANSION

RELATED APPLICATION

This applications claims the benefit of the U.S. Provisional application 60/457,246, filed Mar. 26, 2003, the entirety of which is incorporated by reference.

FIELD OF THE INVENTION

This invention relates to a method for preventing expansion of the myocardial infarct size following a heart attack. It also relates to the reduction or constraining of the dilation of the heart following an infarct. It also relates to pressure-controlled infusion of fluid into the pericardial space of the heart.

BACKGROUND OF THE INVENTION

A Myocardial Infarction (MI) or heart attack, occurs when the blood supply to some part of the heart muscle (myocardium) is abruptly stopped. This is often due to clotting in a coronary blood vessel. Blood supplying the heart muscle comes entirely from two coronary arteries, both lying along the outside surface of the heart. If one of these arteries or any part of one suddenly becomes blocked, the area of the heart being supplied by the artery dies. The death of a portion of the heart muscle is a myocardial infarct, and the amount of the heart affected by the sudden occlusion will determine the severity of the attack. If the heart continues to function, the dead portion is eventually walled off as new vascular tissue supplies the needed blood to adjacent areas.

According to the American Heart Association, in the year 2000 approximately 1,100,000 new myocardial infarctions occurred in the United States. For 650,000 patients this was their first myocardial infarction, while for the other 450,000 patients this was a recurrent event. Two hundred-twenty thousand people suffering MI die before reaching the hospital. Within one year of the myocardial infarction, 25% of men and 38% of women die. Within 6 years, 22% of Men and 46% of women develop chronic heart failure, of which 67% are disabled.

An MI starts when a coronary artery suddenly becomes occluded and can no longer supply blood to the myocardial tissue. When a myocardial infarction occurs, the myocardial tissue that is no longer receiving adequate blood flow dies and is replaced with scar tissue. Within seconds of a myocardial infarction, the under-perfused myocardial cells no longer contract, leading to abnormal ventricular wall motion, high wall stresses within and surrounding the infarct, and depressed ventricular function. The infarct expansion and ventricular remodeling are caused by these high stresses at the junction between the infracted (not contracting) tissue and the normal myocardium. These high stresses eventually kill or severely depress function in the still viable myocardial cells. This results in a wave of dysfunctional tissue spreading out from the original myocardial infarct region.

Left ventricular remodeling is defined as changes in shape and size of the Left Ventricle (LV) that can follow a MI. The process of LV enlargement can be influenced by three independent factors that is, infarct size, infarct healing and LV wall stress. The process is a continuum, beginning in the acute period and continuing through and beyond the late convalescent period. During the early period after MI the infarcted region is particularly vulnerable to distorting forces. This period of remodeling is called infarct expansion. The infarct expansion phase of remodeling starts on the first day of MI (likely several hours after the beginning of the MI) and lasts up to 14 days. Once healed, the infarcted tissue or "scar" itself is relatively non distensible and much more resistant to further deformation. Therefore late enlargement is due to complex alterations in LV architecture involving both infarcted and non-infarcted zones. This late chamber enlargement is associated with lengthening of the contractile regions rather than progressive infarct expansion. Post infarction LV aneurysm (a bulging out of the thin weak ventricular wall) represents an extreme example of adverse remodeling that leads to progressive deterioration of function with symptoms and signs of congestive heart failure.

Effective treatments for MI are acute and can be only implemented immediately after the occlusion of the coronary vessel. The newest approaches include aggressive efforts to restore patency to occluded vessels broadly called reperfusion therapies. This is accomplished through thrombolytic therapy (with drugs that dissolve the thrombus) or increasingly with primary angioplasty and stents. Reopening the occluded artery within hours of the initial occlusion can decrease tissue death, and thereby decrease the total magnitude of infarct expansion, extension, and ventricular remodeling. These treatments are effective but clearly not satisfactory alone. In many cases, patients arrive at the appropriately equipped hospital too late for these acute therapies. In other cases, their best efforts fail to reopen blood vessels sufficiently to arrest expansion of the infarct. These therapies are also associated with considerable risk to the patient and high cost.

Chronic post-infarct treatments include pharmaceuticals such as ACE inhibitors, beta blockers, diuretics, and Ca channel antagonists. These agents have multiple effects, but share in the ability to reduce aortic pressure, and thereby cause a slight decrease in wall stress. These agents have been shown to slow the ventricular remodeling process. Nevertheless, their ability to reduce the infarct expansion is limited by side effects such as hypotension (pathologically low blood pressure) that can be fatal to a patient.

Experimental surgical treatments include approaches to exclude, isolate, or remove the infarct region (such as the Dor procedure). The Dor procedure, also called Endoventricular Patch Plasty, consists in suturing a patch inside the ventricle within the limits of the fibrous scar. Other potential surgical approaches include the application of heat to shrink the infarcted tissue, followed by the suturing of a patch onto the infarcted region.

Other treatments envision surrounding the heart, or a significant portion thereof, with a jacket. Kelley et al ("Restraining infarct expansion preserves LV geometry and function after acute anteroapical infarction," Circulation. 1999; 99: 135-142) tested the hypothesis that restraining expansion of an acute infarction preserves LV geometry and resting function. Pilla et al ("Ventricular Constraint Using the Acorn Cardiac Support Device (CSD) Limits Infarct Expansion in an Ovine Model of Acute Myocardial infarction," Journal of Cardiac Failure 2001; 7 Suppl. 2: 40) described that constraining the whole heart with a surgically placed cup limited the infarct expansion in animals. An experimental CSD device used to restrain the heart in the Pilla study was made by the Acorn Cardiovascular Inc. of St. Paul, Minn. The Acorn device, a textile girdle or so-called "cardiac wrap," is wrapped around both the left and right ventricles, thereby preventing further enlargement of the heart. Description of the Acorn device can be found in the U.S. Pat. No. 5,702,343 "Cardiac reinforcement device" and many patents that derived from it. The CSD device has very limited practical value for the treatment of infarct expansion since it requires major open-heart surgery to install. Once installed, the CSD cannot be removed without exposing the patient to additional risks.

Many more scientific studies show that constraining the heart in the hours and days following the acute MI can reduce the extent of damage to the heart. Benefits exhibited by constraining the heart during and after the infarct expansion can be traced down to the relationship between the changing geometry of the heart and the stress in the heart muscle that forms the ventricular wall. The Law of LaPlace says that wall tension is proportional to the product of intraventricular pressure and ventricular radius.

Wall tension can be thought of as the tension generated by the heart muscle fibers that results in a given intraventricular pressure at a particular ventricular radius. Therefore, when the ventricle needs to generate greater pressure, for example with the increased afterload (aortic pressure) the wall tension is increased. This relationship also shows us that a dilated ventricle (as occurs after an MI or in dilated cardiomyopathy) has to generate increased wall tension to produce the same intraventricular pressure.

Left Ventricle (LV) enlargement must occur after a large infarct in order to maintain or restore cardiac output in the presence of the loss of the significant amount of contracting muscle tissue. The LV enlargement is necessary to compensate for this loss. In fact, an enlarged ventricle can eject a larger stroke volume, despite unchanged fiber shortening. The disadvantage of dilatation is the extra workload imposed on normal, residual myocardium and the increase in wall tension (according to the LaPlace Law), which represent the stimulus for hypertrophy. If hypertrophy is not adequate to match increased tension, then a vicious cycle will start which determines further and progressive dilatation. The described mechanism explains how an infarct that at the end of the expansion process exceeds certain size is likely to trigger the long-term irreversible sequence of hypertrophy, dilation and chronic heart failure leading to disability and death.

In addition to the Acorn CSD device, various existing designs of heart constraining mechanisms are described in detail in the following U.S. Patents:

U.S. Pat. No. 5,702,343 Cardiac reinforcement device
U.S. Pat. No. 6,077,218 Cardiac reinforcement device
U.S. Pat. No. 6,085,754 Cardiac disease treatment method
U.S. Pat. No. 6,123,662 Cardiac disease treatment and device
U.S. Pat. No. 6,126,590 Cardiac reinforcement device
U.S. Pat. No. 6,155,972 Cardiac constraint jacket construction
U.S. Pat. No. 6,165,121 Cardiac reinforcement device
U.S. Pat. No. 6,165,122 Cardiac reinforcement device
U.S. Pat. No. 6,174,279 Cardiac constraint with tension indicator
U.S. Pat. No. 6,193,648 Cardiac constraint with draw string tensioning
U.S. Pat. No. 6,241,654 Cardiac reinforcement devices and methods
U.S. Pat. No. 6,293,906 Delivery of cardiac constraint jacket
U.S. Pat. No. 6,332,863 Heart wall tension reduction kit
U.S. Pat. No. 6,332,864 Heart wall tension reduction apparatus
U.S. Pat. No. 6,375,608 Cardiac reinforcement device
U.S. Pat. No. 6,402,679 External stress reduction device and method
U.S. Pat. No. 6,402,680 Stress reduction apparatus and method
U.S. Pat. No. 6,416,459 Bag for at least partially enveloping a heart
U.S. Pat. No. 6,425,856 Cardiac disease treatment and device
U.S. Pat. No. 6,482,146 Cardiac disease treatment and device
U.S. Pat. No. 6,494,825 System for stress relieving the heart muscle and for controlling heart function.

In spite of the great diversity of shapes, materials and forms, all of these constraint methods and mechanisms are not suited to fulfill the objectives of this invention. The prior cardiac constraints are described as socks, girdles, cups, wraps, bands, belts, bladders and pockets that are surgically placed around the heart, or outside of the pericardium, to prevent it from expanding beyond certain desired size. These devices are intended for chronic treatment to produce benefit over the years in the late stages of ventricular remodeling, long after the infarct expansion stage. All of the prior art devices require major surgery to install. Once installed, they cannot be "turned off" or removed easily.

U.S. Pat. No. 6,463,332 "Method and system for pericardial enhancement" describes a unique method of constraining the heart by changing the properties of the human pericardium. Pericardium is a sac-like membrane that contains the heart. The invention modifies the pericardium to treat patients suffering from or at risk of heart failure to prevent remodeling of the heart. Methods and apparatus are provided for stiffening, strengthening, tightening, reshaping, and/or shrinking the pericardium to enhance the restraining and supporting capability of the pericardium around the heart.

In spite of the great diversity of the described methods of constraining the heart and their proven benefit of the reduction of the infarct expansion there is no demonstrated commercial success or even clinical benefit. The limitations of the known heart constraints are the difficulty and risks of the surgical implantation technique, lack of adjustability and the irreversibility of the implant.

Despite spectacular improvements in MI therapy, within one year of the myocardial infarction, 25% of men and 38% of women die. The total number and incidence of heart failure continues to rise with over 500,000 new cases each year. Approximately 85% of these new cases of heart failure are a direct consequence of a large MI. While considerable progress has been made in acute reperfusion of the heart immediately after the MI, heart remodeling and infarct expansion that follows is not treated effectively. There is a clear clinical need for a novel treatment that can be applied shortly after the MI to reduce the extent of the infarct expansion.

SUMMARY OF THE INVENTION

In one embodiment, the invention reduces the severity and complications of MI by reducing the infarct expansion which may be achieved by reducing stress in the infarcted ventricle by constraining the heart and reducing the diastolic dilation of the heart. The infarct expansion may be reduced with a procedure that is practical, simple, easily reversible, and minimally invasive (does not require general anesthesia and surgery).

Multiple animal studies have established benefit of constraining the heart in hours and days immediately following MI. The purpose of a cardiac constraint is the reduction of the myocardial stress and ventricular dilation.

The inventors overcame the limitations of the existing methods and devices for heart constraining with a novel and counterintuitive technology. The inventive method consists of controllably infusing pressurized fluid into the pericardial sac. The pericardial sac surrounds and encapsulates the heart. Hydraulic pressure exerted by the infused fluid is transmitted to the external walls of the heart. This pressure is distributed over the entire external surface of the heart including the LV. The pressure is controlled to a preset value to avoid significant interference with the filling of the heart. Controlling this pressure is very important. If the pressure exceeds atrial or ventricular diastolic (also called filling) pressure, these structures may collapse. Collapse of the atria or ventricles will cause a limitation in filling of the heart, thus a decrease cardiac output. Decreased cardiac output leading to hypotension is primarily responsible for causing death in the patients. Clearly, controlling the pressure inside the pericardium is paramount and must be high enough to receive a clinical benefit in infarct expansion yet low enough to prevent a clinically significant hemodynamic insult. While it may be possible to set and maintain a constant intrapericardial pressure, it may be advantageous to have additional physiologic sensors to measure such endpoints as cardiac output or systemic blood pressure and adjust the intrapericarial pressure based on these measurements. Additional measures include such things as venous oxygen saturation, pH of the blood, lactate and many other commonly used clinical measures of homeostasis.

A catheter may be place in the pericardial space by performing a minimally invasive surgical procedure. For example, a 2 inch long incision may be made just below the last rib. Though the incision, the pericardium may be easily visualized. A small incision may be made in the pericardium through which the catheter may be placed into the pericardial space.

The pericardial sac can also be accessed with a percutaneous catheter therefore eliminating the need for surgery. Pressure in the pericardial sac can be controlled to ensure that the patient is not in danger. In case of emergency the fluid infused into the pericardial sac can be instantly drained therefore totally reversing the therapy.

The pericardium (also called pericardial sac or pericardial complex) consists of an outer fibrous layer and an inner serous layer. The fibrous pericardium is a flask-shaped, tough outer sac with attachments to the diaphragm, sternum, and costal cartilage. The serous layer is thin and is adjacent to the surface of the heart. The pericardium serves as a protective barrier from the spread of infection or inflammation from adjacent structures. The potential space produced by these layers contains approximately 20 cc of fluid with electrolyte and protein profiles similar to plasma. Approximately 120 cc of additional fluid can accumulate in the pericardium without an increase in pressure. Further fluid accumulation can result in marked increases in pericardial pressure, eliciting decreased cardiac output and hypotension (cardiac tamponade).

Effects of fluid accumulation in the pericardial space are clinically known as a result of the pathological medical conditions known such as pericarditis and cardiac tamponade. Pericarditis and cardiac tamponade are clinical problems involving the potential space surrounding the heart or pericardium. Pericarditis is one cause of fluid accumulation in this potential space; cardiac tamponade is the hemodynamic result of fluid accumulation.

Drainage of pericardial fluid called pericardiocentesis is the definitive treatment of cardiac tamponade. Removal of even a small volume of fluid can rapidly improve blood pressure and cardiac output, and may ultimately prove to be lifesaving. The pericardium can be tapped from almost any reasonable location on the chest wall. However, for the usual "blind" pericardiocentesis, the subxiphoid approach is preferred. Echocardiography is often used to guide needle insertion and the subsequent path of the needle/catheter. The patient may either be recumbent or positioned so that his chest is at a 30-degree angle from the bed. The needle is then inserted into the left xiphocostal angle perpendicular to the skin and 3 to 4 mm below the left costal margin. The needle is advanced directly into the inner aspect of the rib cage; the depth of perpendicular penetration depends on the amount of overlying soft tissue. The hub of the needle is then depressed so that the needle points toward the left shoulder. Using a slow, cautious "warm gear" turning action of the fingers, the needle is advanced about 5 to 10 mm of until fluid is reached.

The invention may be embodied as a "controlled cardiac tamponade" where the moderate tamponade is artificially created by the infusion of fluid into the pericardial sac. To maintain the pressure at the desired level, excess fluid can be drained. Access to the pericardium is achieved using the same techniques as in pericardiocentesis. A catheter may be placed in the pericardial sac and an external system for infusing, adjusting and monitoring pressure in the pericardium. As a result a "hydraulic shell" is temporarily formed around the heart. The shell forms a heart constrictor that does not require surgical implantation and can be easily reversed by draining the fluid from the pericardium. Unlike with the existing mechanical heart constrictors the size of the heart and the anatomic fit are irrelevant.

SUMMARY OF THE DRAWINGS

A preferred embodiment and best mode of the invention is illustrated in the attached drawings that are described as follows.

DETAILED DESCRIPTION OF THE INVENTION

For the proposed clinical use, the capability of the preferred embodiment of the invention is to constrain the heart by controllably elevating hydraulic pressure in the pericardial sac.

Figure 1:
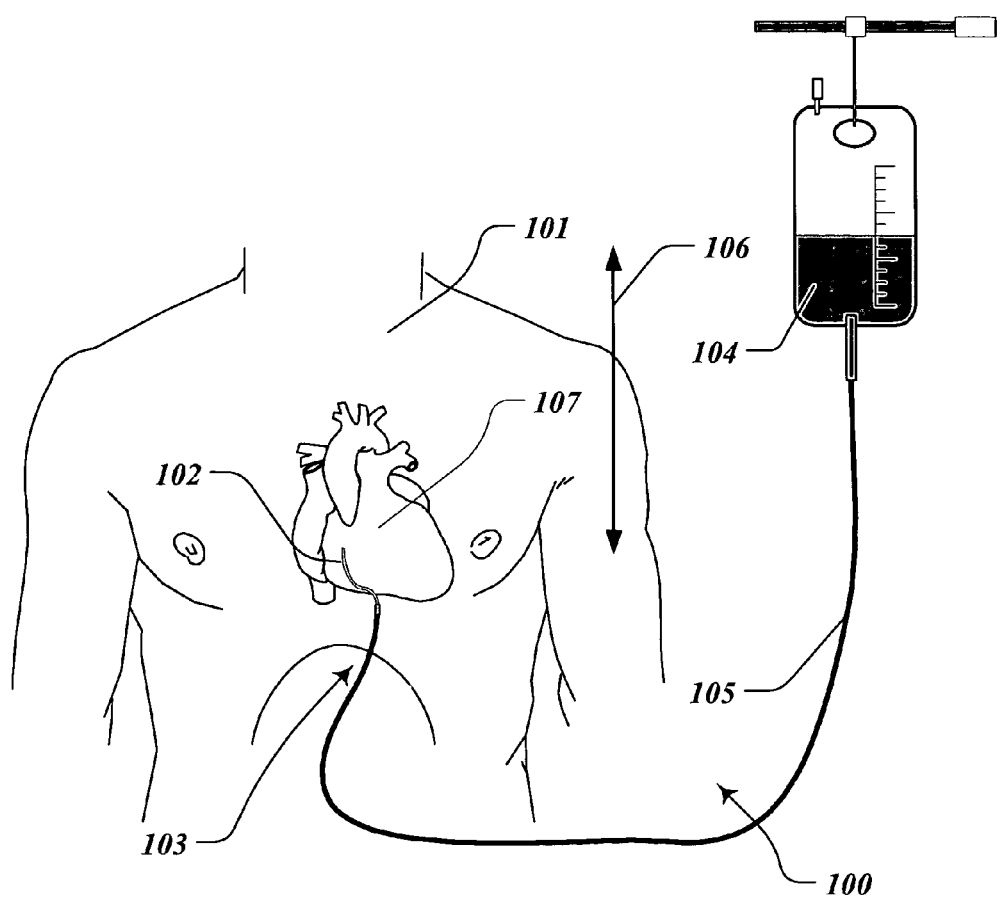
FIG. 1 illustrates the treatment of a patient by infusion of fluid into the pericardium of the heart

FIG. 1 illustrates the treatment of a patient 101 with the system 100 for infusion of fluid into the pericardial sac of the heart. The infusion catheter 102 is partially inserted into the pericardial sac of the heart 107. Catheter 102 crosses the patient's skin in the xiphoid area 103. The distal tip of the catheter 102 has an opening and is in fluid communication with the pericardial (also called intrapericardial) space. The proximal end of the catheter is connected to the bag 104 filled with the hydraulic infusion solution such as sterile saline by the fluid filled tube 105. The height difference 106 between the patient's heart 107 and the level of fluid in the bag determines the hydraulic pressure in the pericardium. For example, if the hydraulic fluid has the specific gravity of water, the height difference 106 equal to 100 cm will generate the hydraulic pressure of 7.35 mmHg. It can be expected that for the efficient and safe constraining of the heart pericardial pressure in the range of 5 to 20 mmHg is desired.

Figure 2:
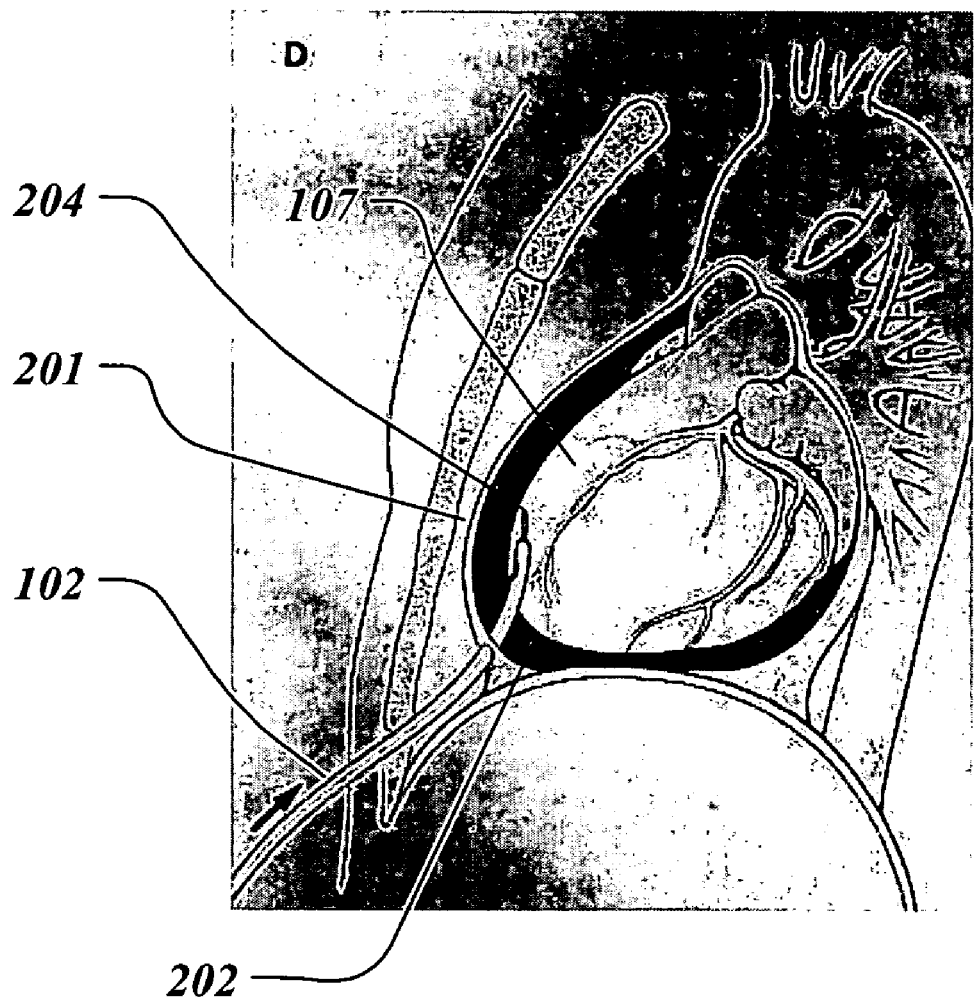
FIG. 2 illustrates the catheter for infusion of fluid into the pericardial sac of the heart

FIG. 2 illustrates the method of the hydraulic heart constraint in greater detail. The catheter 102 is shown percutaneously inserted into the peritoneal space 202 of the heart 107. Distal tip 205 of the catheter resides in the space between the peritoneal sac 201 and the external surface of the heart 107 defined as called pericardial space or intrapericardial space. The peritoneal sac 201 (also called pericardium) is shown punctured by the catheter. Proximal end of the catheter 102 (not shown) is connected to the infusion system outside of the patient's body. The catheter can be inserted into the pericardium sac using the common clinical technique of pericardiocentesis. First the pericardium is tapped with a needle. After the position of the needle is confirmed, the needle is withdrawn and replaced with a soft, pigtail catheter using the Seldinger technique. After dilating the needle track, the catheter is advanced over the guidewire into the pericardial space.

Advanced methods and devices for placement of catheters inside the pericardium sac are described in the U.S. Pat. Nos. 6,423,051 "Methods and apparatus for pericardial access" and 6,162,195 "Method and apparatus for accessing the pericardial space." Soft plastic catheters for infusion of fluids, irrigation and drainage are widely available from many manufacturers of medical devices.

Figure 3:
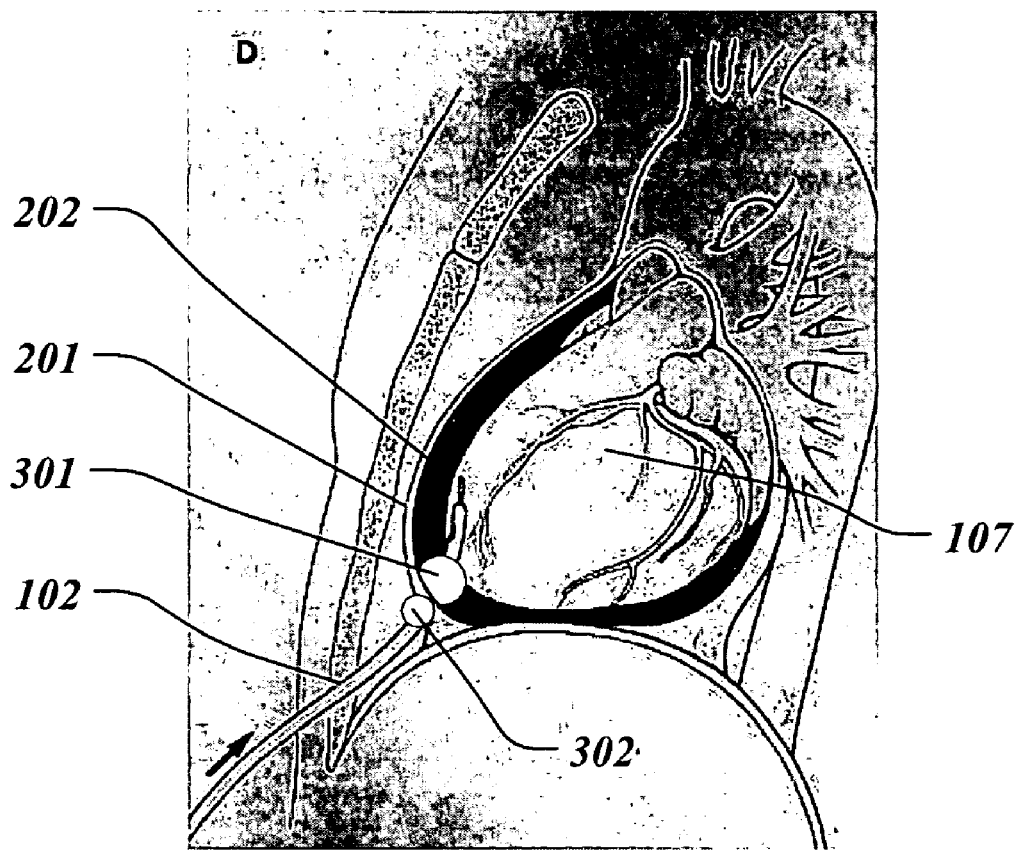
FIG. 3 illustrates the sealing of the puncture in the pericardium

FIG. 3 illustrates an advanced embodiment of the pericardial catheter 102. Fluid in the pericardial space 202 is under hydraulic pressure of 20 mmHg or higher. As a result, the infused fluid can leak around the catheter where the catheter punctures and crosses the pericardium 201. To prevent fluid from leaking out of pericardial sac catheter 102 is equipped with an inflatable balloon seal 301. When the balloon is deflated it is flush with the catheter shaft and can be inserted through a small puncture hole. After the distal catheter tip is positioned in the pericardial sac, the balloon is inflated and the catheter is pulled back by the operator to seal the puncture. Inflated balloon 301 will prevent the catheter 102 from slipping out of the pericardial space by accident. An additional pericardial balloon 302 can be added to the design of the catheter. This balloon is intended to stay outside of the pericardial sac. As a result of the inflation of both balloons the pericardial wall 201 is squeezed tightly between the balloons 301 and 302 and the catheter fixation in place and the sealing of the puncture are improved.

Catheters equipped with inflatable and expandable balloons on the tip are well known in the medical device industry. For example U.S. Pat. No. 6,500,145 "Retrograde cardioplegia catheter" disclosed a catheter having an elongated cannula with an infusion lumen and a pressure-sensing lumen. A balloon is attached to and surrounds the cannula near the distal end while being in fluid communication with the infusion lumen through one or more inflation openings. Another catheter design suitable for the infusion of fluids into the pericardium after simple modifications is described in the U.S. Pat. No. 6,514,228 "Balloon catheter having high flow tip." There are known examples of balloon tipped catheters used to prevent leaks and seal body cavities. For example, U.S. Pat. No. 5,728,134 "Method and apparatus for hemostasis" describes a method of sealing a puncture in a blood vessel. The method including the steps of inserting a catheter with a balloon into the introducer sheath, positioning the balloon against an outside surface of a wall of the artery at the puncture, inflating the balloon against the outside surface of the artery at the puncture, and maintaining the balloon against the puncture so that the balloon substantially seals blood flow from the puncture so as to achieve hemostasis.

Figure 4:
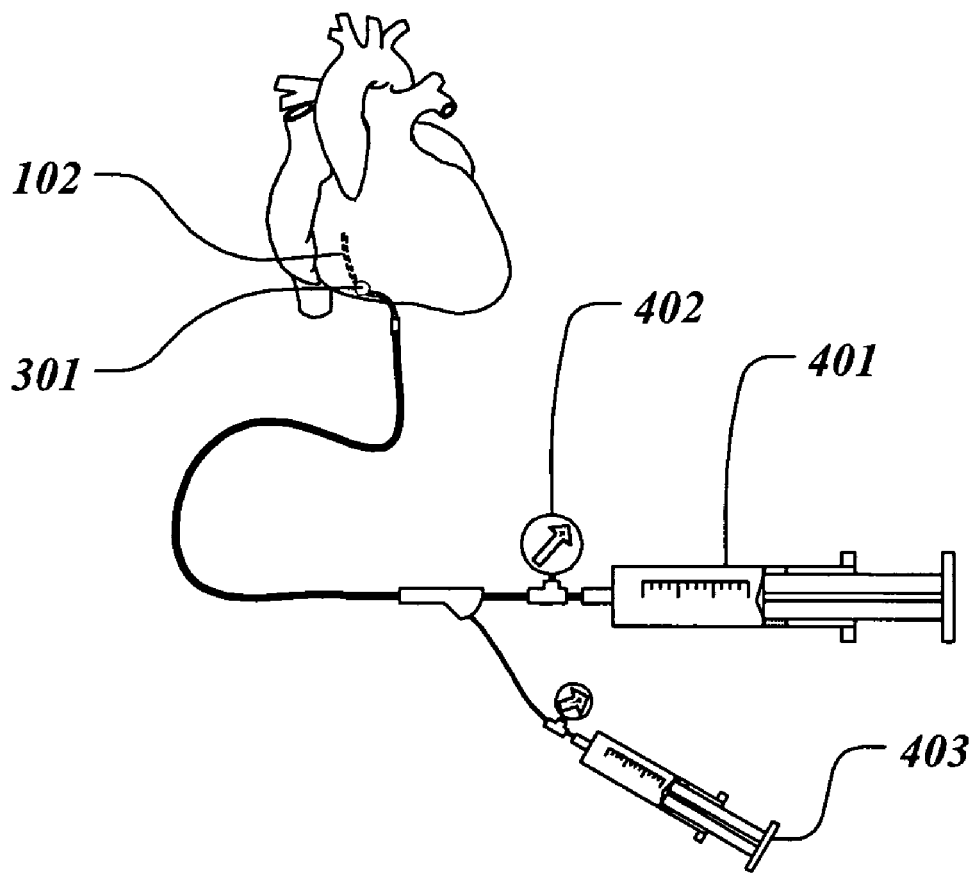
FIG. 4 illustrates an alternative embodiment of the invention

FIG. 4 shows an alternative embodiment of a system for infusion of fluid into the pericardial space of the heart. The infusible fluid is contained in the syringe 401. The infusion catheter 102 is connected to the syringe with a fluid-filled tube. The syringe 401 is equipped with the pressure gage 402 to monitor pressure of fluid in the pericardial sac. Additional syringe 403 can be used to inflate the balloon 301 to seal the pericardium space.

Figure 5:
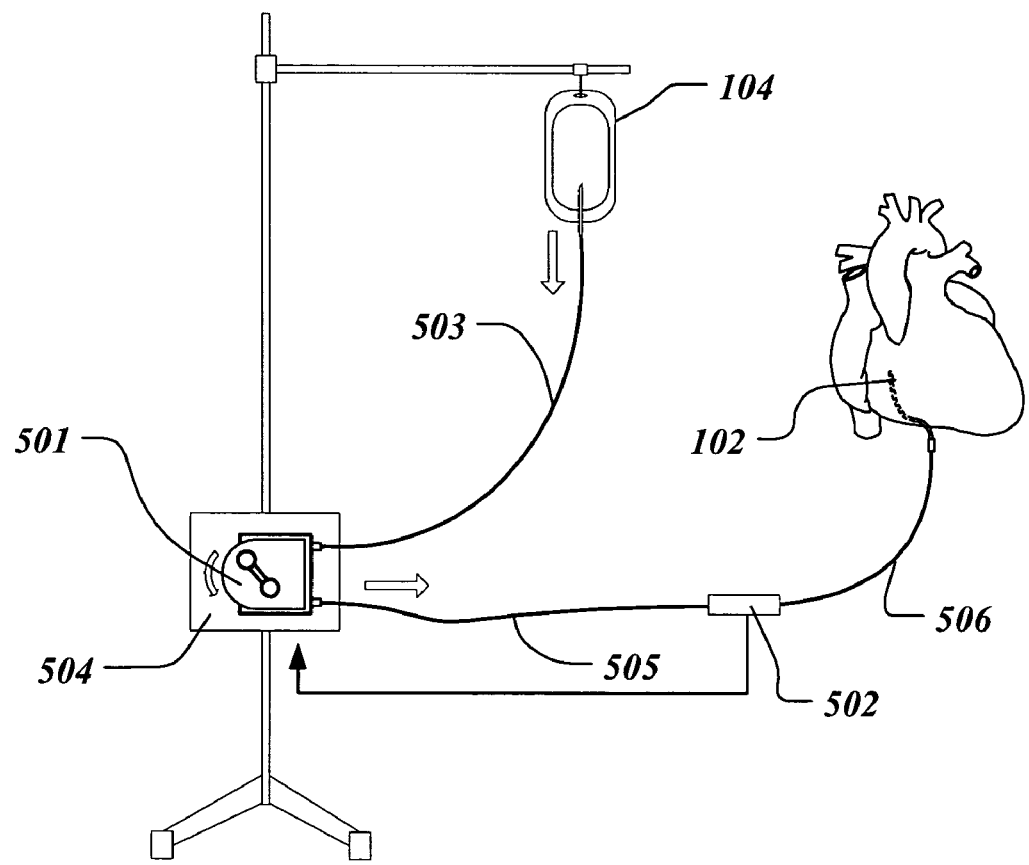
FIG. 5 illustrates an alternative embodiment of the invention with microprocessor controls

FIG. 5 shows a more complex embodiment of the invention. This embodiment may be preferred if more accurate control of the pericardial pressure over longer time is desired. The pericardial catheter 102 is connected to the fluid reservoir 104 via fluid filled tubes 506, 505 and 503. Fluid is infused into and drained from the pericardial sac by the motor controlled pump 501. The pump can be of any type commonly used to infuse IV medicine or to circulate blood. The pump 501 shown as an example is a peristaltic roller pump. Suitable peristaltic roller pump is described, for example, in the U.S. Pat. No. 4,229,299. Pump rotation is controlled by a microprocessor system (not shown) inside the control console 504. The control console receives information from the pressure sensor 503 connected to the fluid tubing 506. Console controls the rotation of the pump based on the received pressure signal. Sensor 502 can be a similar disposable blood pressure sensor (such as ones made by Merit Medical of Utah) that is used widely for invasive blood pressure measurement or similar to compact tube-mounted sensors described in U.S. Pat. Nos. 6,171,253 and 6,272,930.

Figure 6:
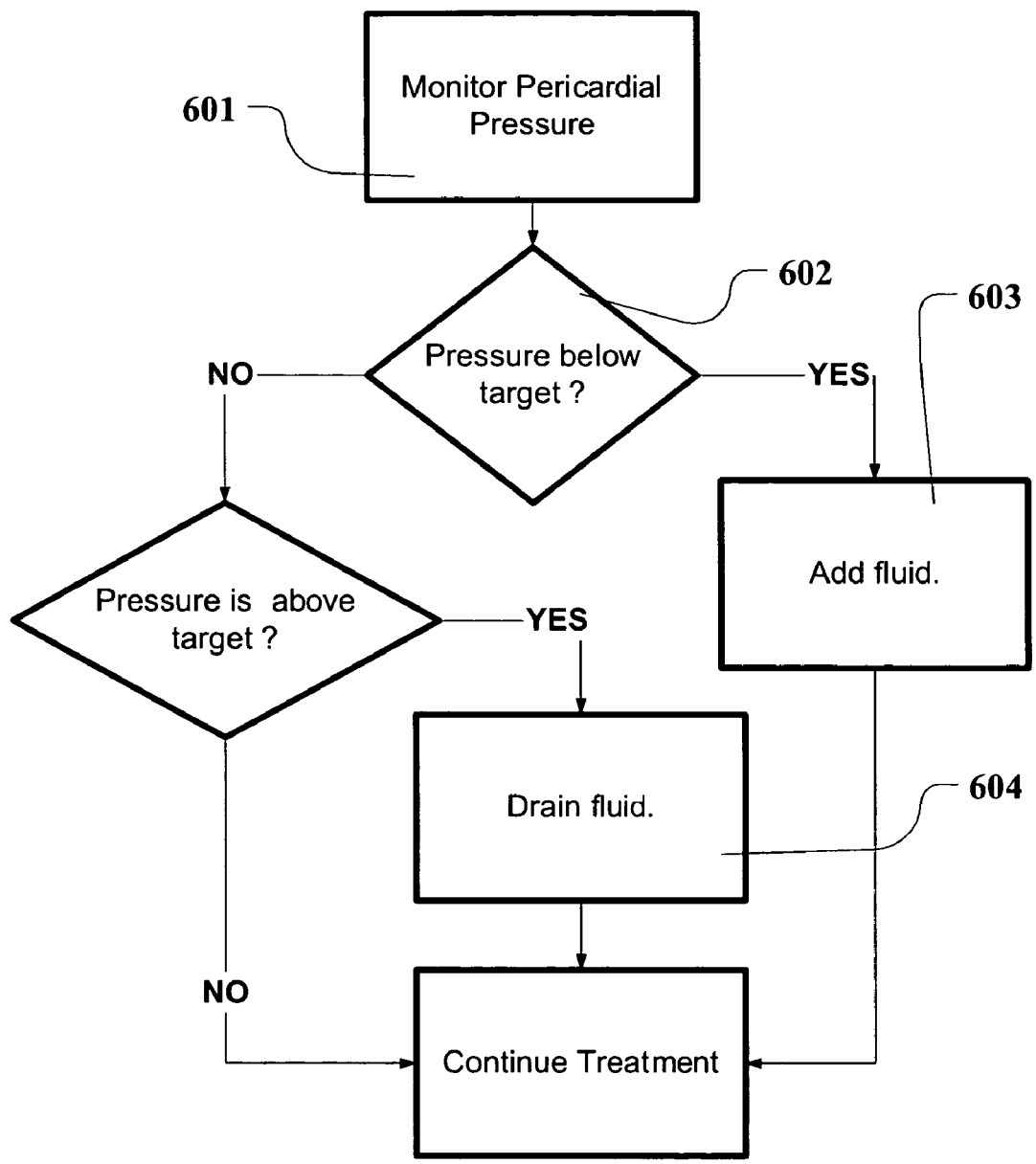
FIG. 6 illustrates an algorithm for controlling the pericardial pressure.

FIG. 6 illustrates a software algorithm embedded in the microprocessor of the control console system 504 (FIG. 5). Pericardial pressure is monitored 601 continuously using a pressure sensor 502 (FIG. 5), an amplifier and an analog-to-digital converter (Not shown). These are the standard components of a digital pressure monitor that need not be explained in detail. The processor is equipped with an internal clock. Information in digital form is supplied to the processor every 5-10 milliseconds. The software algorithm compares 602 the measured pressure to the target value set by the operator or calculated by the processor. The algorithm commands the inflation 603 or deflation 604 of the pericardial space 202 (FIG. 2) with fluid based on the pressure feedback 601 with the objective of achieving the desired pressure target. Generally the goal of the algorithm is to achieve pericardial pressure that is greater than 5 mmHg and less than 20 mmHg. Implementation of the algorithm illustrated by FIG. 6 can be easily achieved by applying methods known in the field of controls engineering. For example, classic process control algorithms such as the Proportional Integral (PI) controller can be used to maintain pressure at the target level. Control signals can be applied continuously or periodically to adjust the volume of fluid in the pericardial sac. It can be expected that during the time of the procedure the pericardium can stretch, leak fluid or that the patient's condition such as the cardiac output and peripheral vascular resistance can change. In response to these changes the pericardial pressure target may change requiring the correction. It can be envisioned that the correction will be made automatically or by the operator based on the readings of pressure manometers but it is often preferred to have an automatic response to save time and increase safety.

The invention has been described in connection with the best mode now known to the applicant inventors. The invention is not to be limited to the disclosed embodiment. Rather, the invention covers all of various modifications and equivalent arrangements included within the spirit and scope of the appended claims. Common to all the embodiments is that fluid is infused into the pericardial sac of a patient suffering from acute MI. Pressure inside the pericardial sac creates the effect of a hydraulic constraint that reduces the stress in the walls of the heart. As a result the infarct expansion and heart muscle remodeling are reduced. Treatment can be reversed at any time by draining the fluid from the pericardium.

What is claimed is:

1. A method for treating a heart in a human patient having a pericardial sac comprising:
   a. inserting only a distal tip of a catheter into the pericardial sac of the patient;
   b. infusing fluid through the catheter into the pericardial sac and increasing a fluid pressure in the pericardial sac;
   c. constraining the heart with the infused fluid and the resulting increased fluid pressure to form at least a partial cardiac tamponade, and
   d. reducing dilation of the heart by the constraint on the heart.

2. The method as in claim 1 further comprising inflating a balloon on a distal end of the catheter inside the pericardial space.

3. The method as in claim 2 wherein the catheter is retained in the pericardial space by the balloon.

4. The method as in claim 1 further comprising monitoring pressure in the pericardium during infusion.

5. The method as in claim 1 further comprising adding or draining the fluid from pericardium to maintain a desired pericardial pressure value.

6. The method as in claim 1 wherein the patient has suffered an occlusion of a major coronary artery.

7. The method as in claim 1 wherein the infusion of fluid is continued for during a period of no greater than 14 days.

8. The method as in claim 1 wherein the infusion of fluid beings within twenty four hours after an infarction of the heart.

9. The method of claim 1 wherein the infusion of fluid is continued at least until reaching a predetermined pressure level.

10. The method as in claim 1 wherein during infusion a fluid pressure increases in the pericardium to a level of 5 to 10 mmHg.

11. A method to constrain a heart of a mammalian patient, wherein the heart is in a pericardial sac, said method comprising:
   a. inserting only a distal section of a catheter into the pericardial sac, wherein the distal section does not surround the heart;
   b. infusing a fluid from the distal section and into the pericardial sac to form at least a partial cardiac tamponade;
   c. increasing a fluid pressure in the pericardial sac by the infusion of the fluid, and
   d. reducing a dilation of the heart by the cardiac tamponade in the pericardial sac.

12. A method as in claim 11 further comprising reducing the fluid pressure in the sac after a treatment period of at least one day and less than fourteen days.

13. A method as in claim 11 further comprising monitoring a pressure of the infused fluid;
   comparing the pressure of the infused fluid to a target pressure; and
   draining at least some of the fluid from the sac if the pressure is above the target pressure.

14. A method as in claim 11 wherein the infused fluid is supplied from a container elevated above the patient at a height of between 68 centimeters (cm) and 272 cm.

15. A method for treating the heart comprising:
   infusing a flowable material into the pericardial sac of the heart, wherein the flowable material flows through a distal tip of a catheter inserted into the pericardial sac and the flowable material contacts tile pericardial sac, wherein only the distal tip of the catheter extends into the pericardial sac,
   continuing the infusing at least until the flowable material in the pericardial sac is a sufficient volume to increase a pressure in the sac to form at least a partial cardiac tamponade, and thereby constrain the heart and reduce diastolic dilation of the heart, and
   reduce dilation of the heart by the constraint on tile heart resulting from the cardiac tamponade.

16. A method as in claim 15 wherein the flowable material is a fluid when infused into the sac.

17. A method as in claim 16 wherein the hydraulic shell is a heart constrictor.

18. A method as in claim 15 wherein the flowable material increases a pressure in the pericardial sac by at least 5 mmHg.

19. A method as in claim 15 wherein the flowable material increases a pressure in the pericardial sac by between 5 mmHg and 30 mmHg.

20. A method as in claim 15 wherein the flowable material is infused under a controlled pressure.

21. A method as in claim 15 wherein the volume of flowable material forms a hydraulic shell in the sac and at least partially around the heart.

22. A method for treating a heart of a mammalian patient, the method comprising:
   infusing a flowable material into a pericardial sac of the heart, wherein the flowable material is inside and in contact with tile pericardial sac, wherein the flowable material is infused from a distal section of a catheter, only the distal section of the catheter extends into the pericardial sac, and the distal section does not surround the heart;
   forming a hydraulic shell around at least a portion of the heart by the infusion of the flowable material into the pericardial sac, wherein the hydraulic shell increases a pressure in the pericardial sac due to the infusion of the flowable material and forms at least a partial cardiac tamponade, and
   constraining the heart with the cardiac tamponade and thereby reducing dilation of the heart.

23. A method as in claim 22 further comprising using a catheter having a tip extending through the pericardial sac and a lumen through which the flowable material passes to infuse the flowable material in the pericardial sac.

24. A method as in claim 23 further comprising extending the catheter tip from an interior of a blood vessel and through a wall of the vessel and the pericardial sac.

25. A method as in claim 24 wherein the catheter includes a seal and the method further comprises applying the seal against the wall to seal a puncture formed by extending the catheter tip through the wall.

26. A method as in claim 25 wherein the seal is an expandable balloon and the seal is applied by expanding the balloon to seal the puncture.

27. A method as in claim 23 further comprising sealing a puncture formed by the tip extending through the pericardial sac.

28. A method as in claim 23 wherein the catheter is placed in the pericardial space by performing a minimally invasive surgical procedure.

29. A method as in claim 23 wherein the catheter of a patient at a xiphoid area of the skin of the patient.

30. A method as in claim 22 wherein the flowable material is a fluid during infusion.

31. A method for treating a heart in a mammalian patient comprising:

extending a catheter through a blood vessel adjacent a pericardial sac of the heart;

puncturing a wall of the blood vessel and the pericardial sac with a distal section of the catheter, wherein only the distal section extends into the pericardial sac and the distal section does not surround the heart;

infusing a flowable material from the distal end of the catheter to the pericardial sac of the heart;

forming a hydraulic shell around at least a portion of the heart, by the infusion of the flowable material into the pericardial sac, wherein the hydraulic shell increases a fluid pressure in the pericardial sac and thereby forms at least a partial cardiac tamponade, and constraining the heart with the cardiac tamponade formed by the hydraulic shell.

32. A method as in claim 31 wherein the hydraulic shell forms a heart constrictor constraining the heart.

33. A method as in claim 31 wherein constraining the heart includes reducing a diastolic dilation of the heart.

34. A method for reducing expansion of an infarct of a heart in a human patient having a dilated heart enclosed inside a pericardial sac comprising:

a. inserting only a distal section of a catheter in the pericardial sac of a patient, wherein the distal section does not surround the heart;

b. infusing the fluid through the catheter into the pericardial sac;

c. infusing sufficient fluid to cover substantially the entire surface of the heart with the fluid and to substantially increase a pressure in the pericardial sac, and d. constraining the heart with the fluid substantially covering the heart to substantially reduce the dilation of the heart, wherein the fluid forms at least a partial cardiac tamponade.

35. A method as in claim 34 wherein constraining the heart avoids a hazardous reduction of at least one of blood pressure and cardiac output.

36. A method for reducing abnormal dilation of a heart to treat at least one of acute myocardial infarction and heart failure conditions, the method comprising:

positioning a fluid infusion device such that at least one opening at a distal section is inside the pericardial sac and a proximal end of the device is outside of the patient, wherein only the distal section extends into the sac and the distal section does not surround the heart, pumping fluid through the device to infuse the fluid into the pericardial sac to increase a pressure in the pericardial sac and form at least a partial cardiac tamponade, constraining the heart with the cardiac tamponade and, sealing the pressurized fluid within the pericardial sac.

37. A method as in claim 36, further comprising:

regulating the constraint of the heart to achieve substantial reduction of dilation of the heart.

38. A method for treating a mammalian patient having a dilated heart enclosed inside a pericardial sac comprising:

a. inserting a distal tip of a catheter into the pericardial sac of the patient, wherein only the distal tip of the catheter enters the pericardial sac;

b. infusing fluid through the catheter into the pericardial sac, wherein an amount of fluid is infused to substantially increase a fluid pressure in the sac and forms at least a partial cardiac tamponade;

c. constraining the heart with the cardiac tamponade to substantially reduce the dilation of the heart, and d. sealing a puncture in the pericardial sac formed to infuse the fluid.

39. A method for treating a dilated heart in a pericardial sac of a mammalian patient, the method comprising:

a. inserting only a distal section of a catheter in the pericardial sac, wherein the distal section does not surround the heart;

b. infusing fluid through the catheter into the pericardial sac, wherein an amount of fluid is infused to substantially increase a fluid pressure in the sac and form at least a partial cardiac tamponade;

c. constraining the heart with the cardiac tamponade to substantially reduce the dilation of the heart, and d. sealing the pericardial sac.

40. A method for treating a patient with dilated heart comprising:

inserting into a pericardial sac surrounding the heart only a distal section of a catheter, wherein the distal section does not surround the heart;

creating a cardiac tamponade of the heart by controlled infusion of a fluid from the distal section of the catheter into the pericardial sac to increase a fluid pressure in the pericardial sac, wherein the fluid is in contact with the pericardial sac;

constricting the heart by the infusion which forms at least a partial cardiac tamponade, and dilating the heart by the constriction of the heart due to the cardiac tamponade.

41. A method for treating a patient with dilated heart comprising:

inserting into a pericardial sac surrounding the heart only a distal section of a catheter and the distal section does not surround the heart;

creating a hydraulic shell around the heart by controlled infusion of a fluid from the distal section of the catheter into the pericardial sac, wherein the fluid is in contact with the pericardial sac and the hydraulic shell increases a fluid pressure in the pericardial sac;

constricting the heart by the infusion which forms at least a partial cardiac tamponade, and dilating the heart by the constriction of the heart due to the cardiac tamponade.

42. A method for treating a mammalian patient having a dilated heart enclosed inside a pericardial sac comprising:

inserting only a distal section of a catheter into the pericardial sac of the patient, wherein the distal section does not surround the heart;

infusing fluid through the catheter into the pericardial sac to increase a fluid pressure in the pericardial sac and form at least a partial cardiac tamponade, and constraining the heart with the cardiac tamponade to substantially reduce the dilation of the heart.

* * * * *